(12) United States Patent  (10) Patent No.: US 8,742,135 B1
Igarashi et al.  (45) Date of Patent: Jun. 3, 2014

(54) COMPOUND AMYCOLAMICIN, METHOD FOR PRODUCING THE SAME, AND USE OF THE SAME

(75) Inventors: Masayuki Igarashi, Tokyo (JP); Ryuichi Sawa, Tokyo (JP); Yoshiko Homma, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 434 days.

(21) Appl. No.: 13/278,269

(22) Filed: Oct. 21, 2011

Related U.S. Application Data (63) Continuation of application No. PCT/JP2009/058210, filed on Apr. 24, 2009.

(51) Int. Cl.
*C07D 403/14* (2006.01)

(52) U.S. Cl.
CPC .................................. *C07D 403/14* (2013.01)
USPC ......................................... 548/518; 514/422

(58) Field of Classification Search
CPC .................................................... C07D 403/14
USPC ......................................... 548/518; 514/422
See application file for complete search history.

(56) References Cited

U.S. PATENT DOCUMENTS 5,391,492 A   2/1995   Hamill et al.

FOREIGN PATENT DOCUMENTS

| JP | 10-114777 | 5/1998 |
| JP | 2004-137175 | 5/2004 |
| WO | 91/16346 | 10/1991 |
| WO | 2005/111055 | 11/2005 |

OTHER PUBLICATIONS

Lebeda, D.P., et al., "*Amycolatopsis kentuckyensis* sp.nov, *Amycolatopsis lexingtonensis* sp. nov. and *Amycolatopsis pretoriensis* sp. nov., isolated from equine placentas," Int. J. Syst. Evol. Microbiol., 2003, vol. 53, p. 1601-1605.
Lechevalier, M.P., et al., "Two New Genera of Nocardioform Actinomycetes: *Amycolata* gen. nov. and *Amycolatopsis* gen. nov.," Int. J. Syst, Bacteriol., 1986, vol. 36, No. 1, p. 29-37.
Sievert, D.M, et al., "*Staphylococcus aureus* Resistant to Vancomycin—United States, 2002," MMWR, Jul. 5, 2002, vol. 51, No. 26, p. 565-567.
Singh, S.B., et al., "Biosynthetic studies of Nocathiacin-I," Tetrahedron Letter, Elsevier, Amsterdam, NL, vol. 49, No. 43, Oct. 20, 2008, pp. 6265-6268.
Singh, S.B., et al., "Antibacterial Evaluations of Thiazomycin," The Journal of Antibiotics, vol. 60, No. 9, 2007, p. 565-571.
Zhang, C., et al., "Isolation, structure, and antibacterial activity of thiazomycin A, a potent thiazolyl peptide antibiotic from *Amycolatopsis fastidiosa*," Bioorganic & Medicinal Chemistry, Pergamon, GB, vol. 16, No. 19, Oct. 1, 2008, pp. 8818-8823.
Sasaki, T., et al., "MJ347-81F4 A & B, Novel Antibiotics from *Amycolatopsis* sp.: Taxonomic Characteristics, Fermentation, and Antimicrobial Activity," Journal of Antibiotics, Japan Antibiotics Research Association, Tokyo, JP, vol. 51, No. 8, Aug. 1, 1998, pp. 715-721.
Igarashi, M., et al., "Pargamicin A, a Novel Cyclic Peptide Antibiotic from *Amycolatopsis* sp.," The Journal of Antibiotics, vol. 61, No. 6, 2008, pp. 387-393.
Nagarajan, R., et al., "M43 Antibiotics: Methylated Vancomycins and Unrearranged CDP-I Analogues," Journal of the American Chemical Society, ACS, US, vol. 110, No. 23, Nov. 1, 1988, pp. 7896-7897.
Platas, G., et al., "Production of antibacterial activities by members of the family *Pseudonocardiaceae*: influence of nutrients," World Journal of Microbiology & Biotechnology, vol. 14, No. 4, 1998, pp. 521-527.

*Primary Examiner* — Robert Havlin
(74) *Attorney, Agent, or Firm* — Carmody Torrance Sandak & Hennessey LLP (57) ABSTRACT

A compound having a structure expressed by the following Structural Formula (1), tautomers thereof, or salts of the compound or the tautomers.

Structural Formula (1)

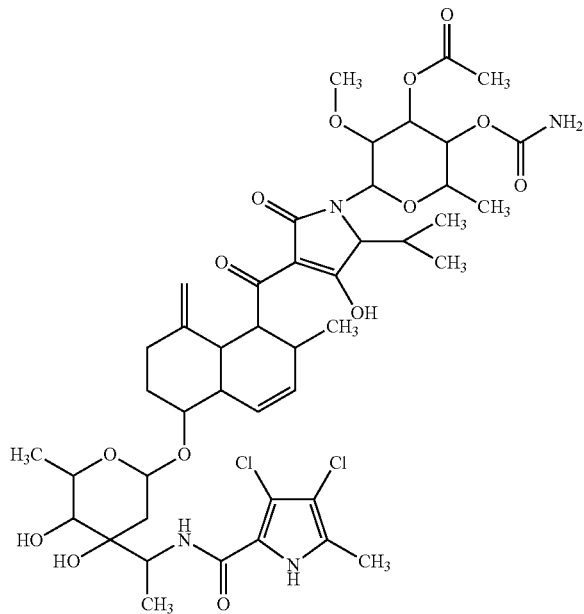

6 Claims, 4 Drawing Sheets

COMPOUND AMYCOLAMICIN, METHOD FOR PRODUCING THE SAME, AND USE OF THE SAME

CROSS-REFERENCE TO RELATED APPLICATION

This is a continuation application of PCT/JP2009/058210, filed on Apr. 24, 2009.

BACKGROUND OF THE INVENTION

1. Field of the Invention

The present invention relates to a new compound having an excellent antibacterial activity against a wide variety of pathogenic bacteria such as drug-resistant bacteria and bacteria causing pneumonia in domestic livestock, a method for producing the new compound, use of the new compound, and a new microorganism that produces the new compound.

2. Description of the Related Art

In general, infectious diseases caused by pathogenic bacteria are treated with chemotherapy including administering drugs such as antibiotics. However, conventionally, frequent use of such drugs has allowed pathogenic bacteria to acquire an ability to neutralize these drugs, leading to appearance of resistant bacteria to which the drugs are ineffective. Actually, many drug-resistant bacteria have been problematic mainly in medical facilities.

For example, as one clinically important problem, *Staphylococcus aureus*, which is known as bacteria causing suppurative diseases, pneumonia and food poisoning, acquires multidrug resistances to methicillin or other antibiotics to be methicilline-resistant *Staphylococcus aureus* (MRSA). At present, vancomycin, teicoplanin, arbekacin, line zolid, etc. are used as typical therapeutic drugs against MRSA. However, it is generally difficult to completely eliminate MRSA. In particular, thorough care should be taken about the use of vancomycin, since appearance of vancomycin resistant *Staphylococcus aureus* (VRSA) has already been reported (see Sievert D M, et al.: *Staphylococcus aureus* Resistant to Vancomycin United States, 2002. MMWR Jul. 5, 2002; 51: 565-567.).

In order to overcome such problems relating to drug-resistant bacteria, demand has arisen for the development of a new compound that has a different chemical structural skeleton from those of the conventional antibiotics and also has an excellent antibacterial activity.

Furthermore, infectious diseases caused by pathogenic bacteria can be greatly problematic in not only human but also non-human animals. For example, pneumonia in domestic livestock such as bovine and pig is expected to effectively prevent or treat in the livestock industry. Therefore, at present, further demand has arisen for the development for a new compound having an excellent antibacterial activity against bacteria causing pneumonia in domestic livestock.

BRIEF SUMMARY OF THE INVENTION

The present invention aims to solve the above existing problems and achieve the following objects. That is, an object of the present invention is to provide a new compound having an excellent antibacterial activity against a wide variety of pathogenic bacteria such as drug-resistant bacteria and bacteria causing pneumonia in domestic livestock, tautomers thereof, or salts of the new compound or the tautomers; a method for producing them; a new microorganism that produces the new compound, the tautomers thereof, or the salts of the new compound or the tautomers; and an antibacterial agent containing the new compound, the tautomers thereof, or the salts of the new compound or the tautomers.

In order to solve the above existing problems, the present inventors conducted extensive studies to succeed in isolating as a new microorganism a bacterial strain belonging to the genus *Amycolatopsis*, and have found that this bacterial strain produces an antibiotic having a new structural skeleton. The present inventors have found that this antibiotic has an excellent antibacterial activity against a wide variety of pathogenic bacteria such as drug-resistant bacteria and bacteria causing pneumonia in domestic livestock, and have also confirmed that this antibiotic is a new compound through analysis of its chemical structure. The present invention has been accomplished on the basis of these findings. Notably, the present inventors named this new compound "amycolamicin."

The present invention is based on the above findings obtained by the present inventors. Means for solving the above existing problems are as follows.

<1> A compound having a structure represented by the following Structural Formula (1), tautomers thereof, or salts of the compound or the tautomers.

Structural Formula (1)

<2> A method for producing the compound, the tautomers or the salts according to <1>, the method including:

culturing a microorganism belonging to the genus *Amycolatopsis* and capable of producing the compound, the tautomers or the salts according to <1>, and isolating the compound, the tautomers or the salts according to <1> from a culture obtained from the culturing.

<3> The method according to <2>, wherein the microorganism is a microorganism of *Amycolatopsis* sp. MK575-fF5 strain deposited under accession number FERM P-21465.

<4> A microorganism, wherein the microorganism belongs to the genus *Amycolatopsis* and is capable of producing the compound, the tautomers or the salts according to <1>.

<5> The microorganism according to <4>, wherein the microorganism is a microorganism of *Amycolatopsis* sp. MK575-fF5 strain deposited under accession number FERM P-21465.

<6> An antibacterial agent including:

the compound, the tautomers or the salts according to <1> serving as an active ingredient.

The present invention can provide a new compound having an excellent antibacterial activity against a wide variety of pathogenic bacteria such as drug-resistant bacteria and bacteria causing pneumonia in domestic livestock, tautomers thereof, or salts of the compound or the tautomers; a method for producing the new compound, the tautomers thereof, or the salts of the new compound or the tautomers; a new microorganism that produces the new compound, the tautomers thereof, or the salts of the new compound or the tautomers; and an antibacterial agent containing the new compound, the tautomers thereof, or the salts of the new compound or the tautomers. These can solve the above existing problems and achieve the above objects.

DETAILED DESCRIPTION OF THE INVENTION

Compound, Tautomers Thereof, or Salts of the Compound or the Tautomers

A compound of the present invention has a structure expressed by the following Structural Formula (1). The compound having the following Structural Formula (1) is a new compound separated by the present inventors (hereinafter may be referred to as "amycolamicin").

(1) Appearance: white powder (2) Molecular formula: $C_{44}H_{60}Cl_2N_4O_{14}$ (3) High resolution mass spectrometry (HRESIMS: negative ion mode)

Calcd: m/z 937.3386 (M-H)$^-$

Found: m/z 937.3405 (as $C_{44}H_{59}Cl_2N_4O_{14}$)

(4) Specific rotation $[\alpha]_D^{23}=-21.6°$ (c 0.5, methanol)

Figure 1:
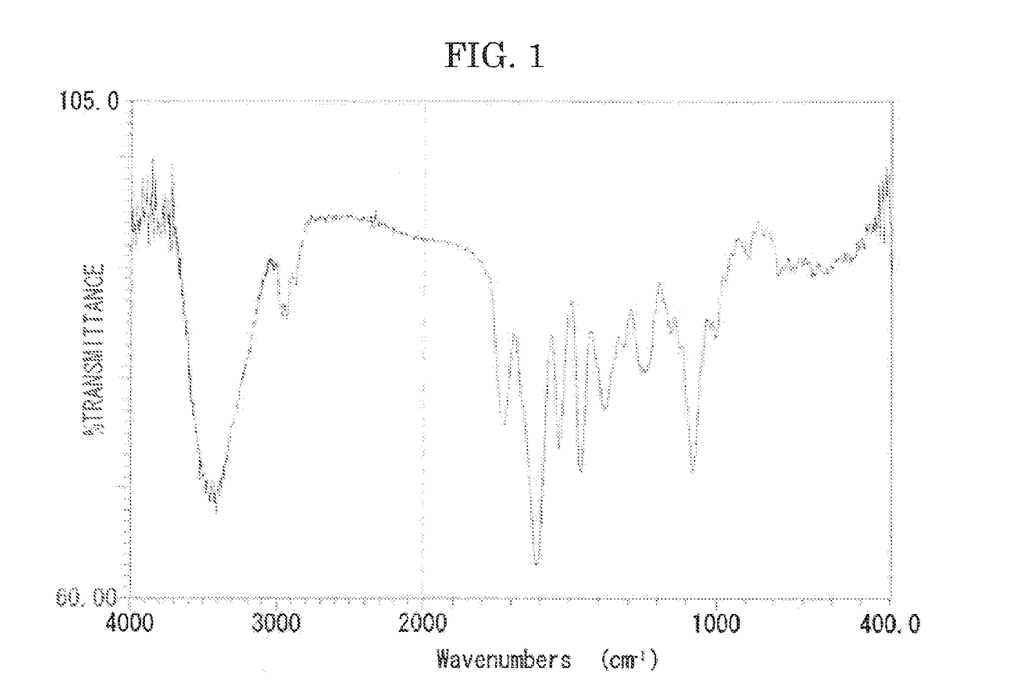
FIG. 1 is an infrared absorption spectrum chart of amycolamicin measured by the KBr tablet method, where vertical axis: transmittance (%) and horizontal axis: wavenumber ($cm^{-1}$).

(5) Infrared absorption spectrum is as shown in FIG. 1.

Figure 2:
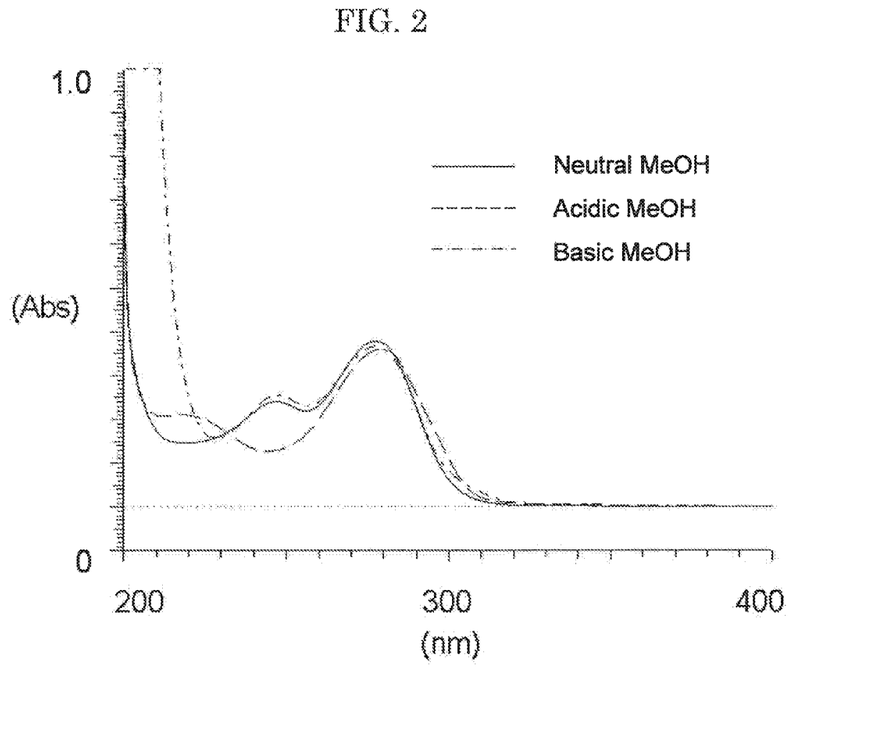
FIG. 2 is a UV absorption spectrum chart of amycolamicin measured in methanol, where vertical axis: absorbance (Abs) and horizontal axis: wavelength (nm).

(6) UV absorption spectrum is as shown in FIG. 2.

Figure 3:
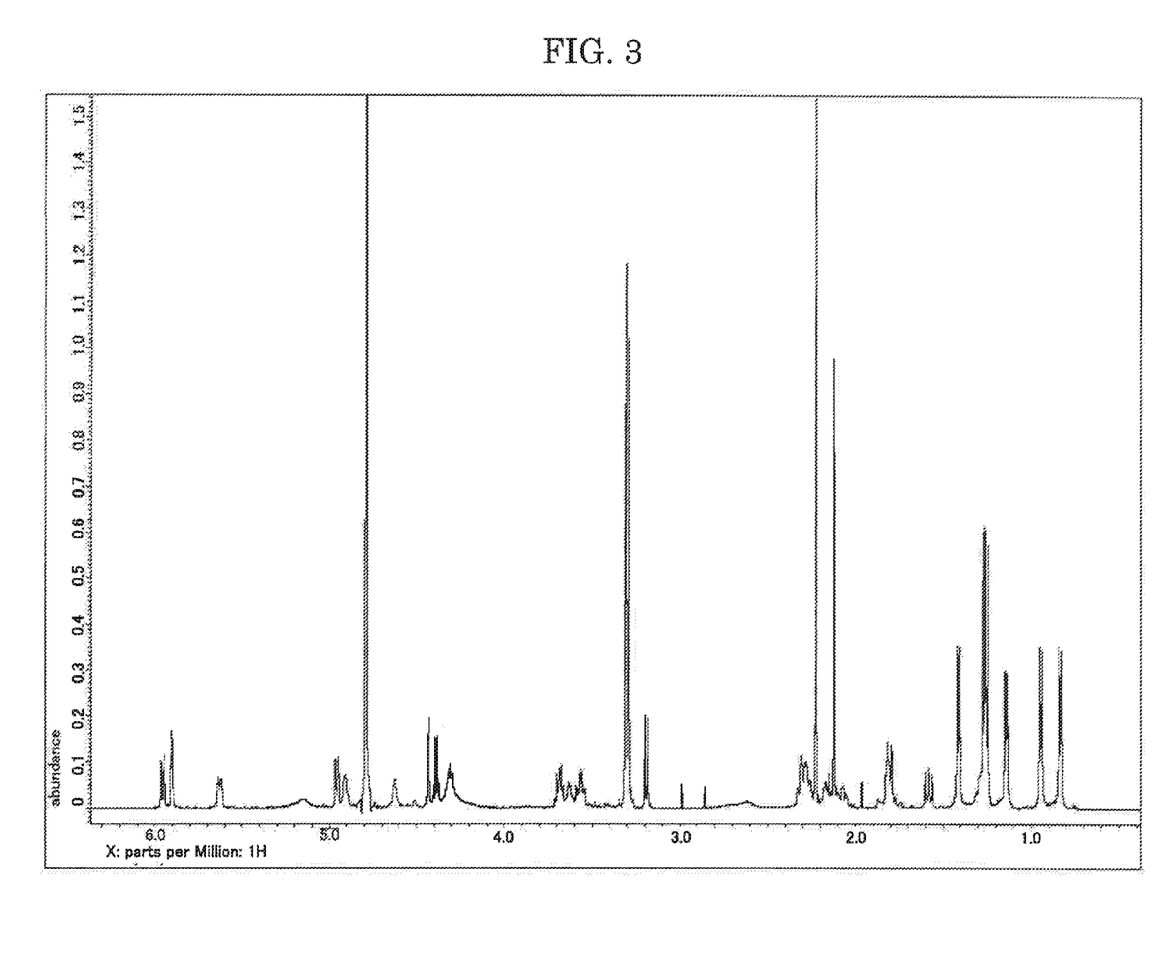
FIG. 3 is a $^1H$ nuclear magnetic resonance spectrum chart of amycolamicin measured in deuterated methanol at 30° C. and 600 MHz, where the unit of the horizontal axis: ppm.

(7) $^1H$ nuclear magnetic resonance (NMR) spectrum measured in deuterated methanol at 30° C. and 600 MHz is as shown in FIG. 3.

Figure 4:
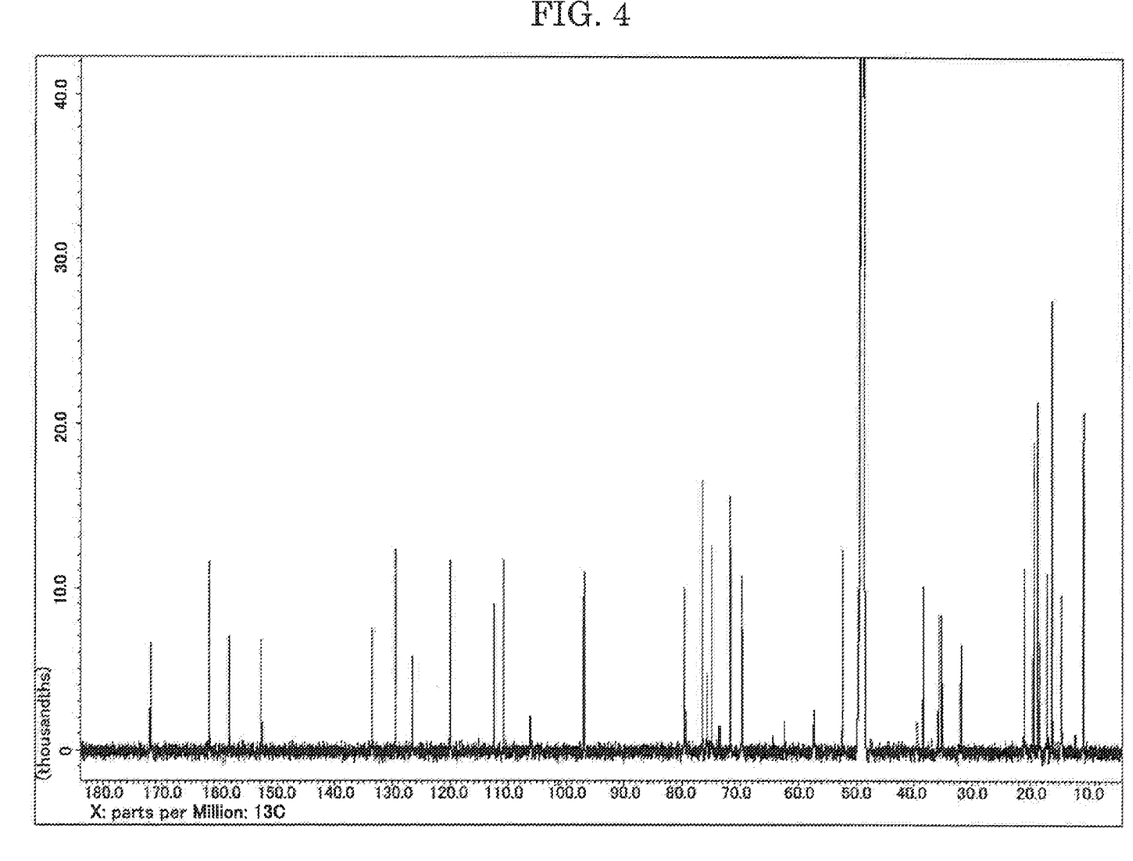
FIG. 4 is a $^{13}C$-NMR spectrum chart of amycolamicin measured in deuterated methanol at 30° C. and 150 MHz, where the unit of the horizontal axis: ppm.

(8) $^{13}C$ nuclear magnetic resonance (NMR) measured in deuterated methanol at 30° C. and 150 MHz is as shown in FIG. 4.

(9) Thin-layer chromatography using silica gel $60F_{254}$ (product of Merck Co.) and a developing solvent of chloroform:methanol (9:1 by volume), the Rf value is 0.31.

Whether a compound has a structure expressed by Structural Formula (1) can be determined with appropriately selected various analysis methods. This determination can be performed by measuring the above $^1H$ nuclear magnetic resonance spectrum, $^{13}C$ nuclear magnetic resonance spectrum, infrared absorption spectrum or mass spectrum.

Notably, amycolamicin has tautomerism and thus encompasses tautomers thereof. Non-limiting examples of the tautomers of amycolamicin include those having the following four Structural Formulas. Amycolamicin can have such several different structural patterns, and is not considered that it exists at a certain fixed state.

Structural Formula (1)

Physico-chemical properties of the compound having the above Structural Formula (1) (i.e., amycolamicin) are as follows.

The spectrum charts of amycolamicin obtained through $^1$H nuclear magnetic resonance spectrum analysis, $^{13}$C nuclear magnetic resonance spectrum analysis, etc. may be somewhat different from those shown in FIGS. 3 and 4. Here, those skilled in the art can easily understand that the compound having Structural Formula (1) can actually have several different structural patterns and does not exist at a certain fixed state. Thus, even when a compound shows a $^1$H nuclear magnetic resonance spectrum chart somewhat different from that of FIG. 3, a $^{13}$C nuclear magnetic resonance spectrum chart somewhat different from that of FIG. 4, and other somewhat different spectrum charts, those skilled in the art could easily identify the compound as amycolamicin.

Also, the amycolamicin may be in the form of a salt. The salt is not particularly limited and may be appropriately selected depending on the intended purpose. Examples thereof include salts formed with alkali metals such as sodium and potassium; salts formed with alkaline earth metals such as calcium and magnesium; and salts formed with organic amines such as methylamine, ethylamine and diethanolamine.

The amycolamicin, tautomers thereof, or salts of the amycolamicin or the tautomers may be produced from the bacteria that produce the amycolamicin or may be obtained through chemical synthesis. Among them, the amycolamicin, the tautomers thereof, or the salts of the amycolamicin or the tautomers are preferably obtained by the below-described method of the present invention for producing the compound, the tautomers thereof, or the salts of the compound or the tautomers.

As shown in Test Examples 1 to 4 described below, the amycolamicin, the tautomers thereof, or the salts of the amycolamicin or the tautomers each have an excellent antibacterial activity against a wide variety of Gram-positive and negative bacteria such as drug-resistant bacteria and bacteria causing pneumonia in domestic livestock. Thus, any of the amycolamicin, tautomers thereof and salts of the amycolamicin and tautomers can be suitably used as, for example, an active ingredient of the below-described antibacterial agent of the present invention.

(Method for Producing Compound, Tautomers Thereof, or Salts of the Compound or Tautomers)

A method for producing the compound of the present invention; i.e., amycolamicin, the tautomers thereof, or the salts of the compound or the tautomers includes: culturing a microorganism belonging to the genus *Amycolatopsis* and capable of producing the amycolamicin, the tautomers thereof, or the salts of the amycolamicin or the tautomers; and isolating the amycolamicin, the tautomers thereof, or the salts of the amycolamicin or the tautomers from a culture obtained from the culturing. Notably, the amycolamicin obtained through culturing of the microorganism may be referred to as "antibiotic amycolamicin" hereinafter.

The antibiotic amycolamicin is produced as follows. Specifically, microorganisms that produce the antibiotic amycolamicin (hereinafter may be referred to simply as "amycolamicin-producing microorganisms") are inoculated into a nutrient medium and cultured at a temperature suitable for the production of the antibiotic amycolamicin, whereby a culture containing the antibiotic amycolamicin is obtained.

The nutrient medium used for the above culturing is nutrient media that can be used for culturing actinomycetes. Examples of the nutrient sources added to the nutrient medium include nitrogen sources such as commercially available soy flour, peptone, yeast extract, meat extract, corn steep liquor and ammonium sulfate; carbohydrates such as tomato paste, glycerin, starch, glucose, galactose and dextrin; and carbon sources such as fats. In addition, inorganic salts such as sodium chloride and calcium carbonate may be added to the medium before use. If necessary, a trace amount of a metal salt may be added to the medium before use. Any known material for culture may be used so long as the material can be utilized by the amycolamicin-producing microorganisms to promote the production of the antibiotic amycolamicin.

The production of the antibiotic amycolamicin uses the microorganism belonging to the genus *Amycolatopsis* and capable of producing the antibiotic amycolamicin. Specifically, it has been clarified that a microorganism of *Amycolatopsis* sp. MK575-fF5 strain isolated by the present inventors (FERM P-21465, details will be described in the following section "Microorganism" of the present invention) can produce the antibiotic amycolamicin. Also, other strains that are capable of producing the antibiotic amycolamicin can be isolated from the natural world by a routine method for isolating bacteria that produce antibiotics. Notably, through mutation treatments such as exposure to radiation, the microorganism of *Amycolatopsis* sp. MK575-fF5 strain and other microorganisms capable of producing the antibiotic amycolamicin can be mutated so that they have increased production capability of the antibiotic amycolamicin. Moreover, the antibiotic amycolamicin can be produced through genetically engineering techniques.

The seed culture used for the production of the antibiotic amycolamicin may be, for example, the growth culture obtained through slant culturing of the amycolamicin-producing bacteria on an agar medium. For the production of the antibiotic amycolamicin, it is preferred that the amycolamicin-producing bacteria be aerobically cultured in an appropriate medium. Also, for isolating the target compound from the resultant culture, a routine method can be used. The culturing temperature is not particularly limited and may be determined depending on the type of the amycolamicin-producing microorganisms, so long as the growth of the amycolamicin-producing microorganisms is not substantially inhibited and the amycolamicin-producing microorganisms can produce the antibiotic amycolamicin. The culturing temperature is preferably 25° C. to 35° C.

For example, the production of the antibiotic amycolamicin by the *Amycolatopsis* sp. MK575-fF5 strain generally becomes maximum for 3 days to 9 days. In general, it is preferred that the production of the antibiotic amycolamicin be performed until the medium exhibits sufficient antibacterial activity. A change over time of the titer of the antibiotic amycolamicin in the culture can be measured through, for example, HPLC or a cylinder plate method using *Staphylococcus aureus* or other bacteria as tested bacteria.

In the above production method, the antibiotic amycolamicin is isolated from the obtained culture. The isolation method may appropriately utilize a method used for recovering metabolites produced by microorganisms. Examples of the isolation method for the antibiotic amycolamicin include a method by extracting with a water-immiscible solvent, a method utilizing differences in adsorption affinity to various adsorbents, gel filtration, chromatography utilizing countercurrent distribution and combinations thereof. The separated microorganisms are treated with an extracting method using an appropriate organic solvent or an eluting method through disruption of microorganisms, whereby the antibiotic amycolamicin can be recovered through extraction of the microorganisms and isolation/purification as described above.

The production method can be performed as described above to produce the antibiotic amycolamicin or the tautomers thereof.

Since the amycolamicin or tautomers thereof are each an acidic compound, the salts of the amycolamicin or tautomers thereof can generally be produced by a known method using, for example, pharmaceutically acceptable various metals (e.g., alkali metals) or organic bases (e.g., quaternary ammonium salts).

(Microorganism)

A microorganism of the present invention belongs to the genus *Amycolatopsis* and is capable of producing the above-described compound of the present invention; i.e., amycolamicin, the tautomers thereof, or the salts of the amycolamicin or the tautomers. The microorganism is not particularly limited and may be appropriately selected depending on the intended purpose, so long as it belongs to the genus *Amycolatopsis* and is capable of producing the amycolamicin, the tautomers thereof, or the salts of the amycolamicin or the tautomers, and thus can be used as the amycolamicin-producing microorganisms in the above-described production method for the compound of the present invention, the tautomers thereof, or the salts of the compound or the tautomers.

In particular, preferably used are actinomycetes isolated from the soil of Sendai-shi, Miyagi and given accession number MK575-fF5 strain in May, 1996 by the microbial chemistry research center of Microbial Chemistry Research Foundation. The mycological characteristics of the MK575-fF5 strain are as follows.

1. Morphology

Substrate hyphae are well branched in a zig-zag form and are divided. Aerial hyphae are grown in some cases or not grown in other cases. When aerial hyphae are grown, the aerial hyphae are relatively long and linear or irregularly curved as well as divided into cylindrical spores. The surface is smooth and the size is about 0.4 μm to 0.6 μm×0.8 μm to 2.2 μm. Also, the aerial hyphae may be tangled together to have a spherical shape. Whorls, mycelial strands, sporangia and motile spores are not observed.

2. Growth Conditions in Various Media

The standards in blankets relating to colors are based on the color harmony manual of Container Corporation of America.

(1) Yeast-Malt Agar Medium (ISP-Medium 2, Culturing at 27° C.)

This strain is grown in pale yellow [2 gc, Bamboo] and slightly forms white aerial hyphae in some cases or does not form them in other cases. Soluble dyes are not produced.

(2) Oatmeal Agar Medium (ISP-Medium 3, Culturing at 27° C.)

This strain is grown in pale yellow [2 gc, Bamboo] and slightly forms white aerial hyphae in some cases or does not form them in other cases. Soluble dyes are not produced.

(3) Starch-Inorganic Salt Agar Medium (ISP-Medium 4, Culturing at 27° C.)

This strain is grown in pale yellow [2 ea, Lt Wheat] to dull yellow [3 nc, Amber] and slightly forms white aerial hyphae in some cases. Soluble dyes are not produced.

(4) Glycerin-Asparagine Agar Medium (ISP-Medium 5, Culturing at 27° C.)

This strain is grown in dull yellowish orange [3 lc, Amber] and forms aerial hyphae of pale orange [4 ea, Light Apricot] in some cases or does not form them in other cases. Soluble dyes are not produced.

(5) Tyrosine Agar Medium (ISP-Medium 7, Culturing at 27° C.)

This strain is grown in pale yellow [3 ca, Pearl Pink] to dull yellowish orange [3 lc, Amber] and forms aerial hyphae of pale orange [4 ca, Fresh Pink] in some cases or does not form them in other cases. Soluble dyes are not produced.

(6) Sucrose-Nitrate Agar Medium (Culturing at 27° C.)

This strain is grown in colorless to pale yellowish orange [3 ea, Lt Melon Yellow] and slightly forms white aerial hyphae in some cases or does not form them in other cases. Soluble dyes are not produced.

3. Physiological Properties (1) Temperature Range of Growth

This strain was cultured on a glucose-aspartic acid agar medium (glucose: 1.0%, L-aspartic acid: 0.05%, dipotassium hydrogenphosphate: 0.05%, string agar: 3.0%, pH 7.0) at a temperature of 10° C., 20° C., 24° C., 27° C., 30° C., 37° C., 45° C. or 50° C. As a result, the strain was not grown at 10° C., 45° C. or 50° C. but was grown at 20° C. to 37° C. The optimal growth temperature is about 30° C.

(2) Hydrolysis of Starch (Starch-Inorganic Salt Agar Medium, ISP-Medium 4, Culturing at 27° C.)

Negative on day 21 from the beginning of the culturing (3) Production of Melanine-Like Dye (Tripton-Yeast-Broth, ISP-Medium 1; Peptone-Yeast-Iron Agar Medium, ISP-Medium 6; Tyrosine Agar Medium, ISP-Medium 7; Culturing at 27° C. For Each Medium)

Negative for each medium (4) Availability of Carbon Source (Pridham-Godleave Agar Medium, ISP-Medium 9; Culturing at 27° C.)

This strain is grown by utilizing D-glucose, L-arabinose, D-xylose, D-fructose, sucrose, inositol, rhamnose, raffinose and D-mannitol.

(5) Reduction Reaction of Nitrate (0.1% Potassium Nitrate-Containing Peptone Water, ISP-Medium 8, Culturing at 27° C.)

Positive

4. Microbial Components (1) Composition of Cell Wall

The cell wall contains meso-2,6-diaminopimelic acid.

(2) Reducing Sugar in Each Microorganism

Each microorganism contains arabinose and galactose (Type A).

(3) Isoprenoid Quinone

MK-9 ($H_4$) and a small amount of MK-10 ($H_4$) are contained as main menaquinone.

(4) Phospholipid

Type PII (phosphatidylethanolamine is contained but phosphatidyl choline and unknown glucosamine-containing phospholipids are not contained)

(5) Mycolic Acid

Not contained.

5. Analysis of 16S rRNA Gene

A partial nucleotide sequence (1,455 nt) of the 16S rRNA gene was determined and searched for homology based on international nucleotide sequence database (GenBank/DDBJ/EMBL). As a result, the nucleotide sequence of the MK575-fF5 strain was found to have high homology with those of the 16S rRNA genes of actinomycetes belonging to the genus *Amycolatopsis*; i.e., *Amycolatopsis kentuckyensis* (99.1%), *Amycolatopsis rifamycinica* (99.03%), *Amycolatopsis mediterranei* (98.9%), *Amycolatopsis balhimycetica* (98.82%), etc. Note that the values in parentheses are homology between the nucleotide sequences.

In summary, substrate hyphae of the MK575-fF5 strain are in a zig-zag form and divided. Aerial hyphae are linear or irregularly curved and divided into cylindrical spores. Whorls, mycelial strands, sporangia and motile spores are not observed. The MK575-fF5 strain is grown in colorless to yellowish orange in various media. Aerial hyphae of white to pale orange are formed in some cases or not formed in other cases. Soluble dyes are not produced. The optimal growth temperature is about 30° C. This strain is negative in terms of the production of melanine-like dye and the hydrolysis of starch, but is positive in terms of reduction reaction of nitrate.

Regarding the microbial components of the MK575-fF5 strain, the hydrolyzates of each microorganism contain meso-2,6-diaminopimelic acid, arabinose and galactose, the cell wall is of Type IV, and the reducing sugars of each microorganism are of Type A. Also, mycolic acid is not contained and phospholipid is of Type PII (phosphatidylethanolamine is contained but phosphatidyl choline and unknown glucosamine-containing phospholipids are not contained) as well as a main menaquinone is MK-9($H_4$).

Through comparison of the partial nucleotide sequence of the 16S rRNA gene with corresponding data of known bacterial strains, the nucleotide sequence was found to have high homology with those of actinomycetes belonging to the genus *Amycolatopsis*.

In conclusion, the MK575-fF5 strain was thought to belong to the genus *Amycolatopsis* (International Journal of Systematic Bacteriology, Vol. 36, pp. 29-37, 1986). Then, the MK575-fF5 strain was designated *Amycolatopsis* sp. MK575-fF5 strain. Notably, the MK575-fF5 strain was requested for deposition to the National Institute of Advanced Industrial Science and Technology, International Patent Organism Depositary and was accepted as FERM P-21465 on Dec. 12, 2007.

(Antibacterial Agent)

An antibacterial agent of the present invention contains, as an active ingredient, the above-described compound of the present invention; i.e., amycolamicin, the tautomers thereof, or the salts of the amycolamicin or the tautomers; and, if necessary, further contains other ingredients.

The amount of the amycolamicin, the tautomers thereof, or the salts of the amycolamicin or the tautomers contained in the antibacterial agent is not particularly limited and may be appropriately selected depending on the intended purpose. The antibacterial agent may be the amycolamicin, the tautomers thereof, or the salts of the amycolamicin or the tautomers, itself or themselves.

The other ingredients are not particularly limited and may be appropriately selected depending on the intended purpose from, for example, pharmacologically acceptable carriers. Examples of the other ingredients include ethanol, water and starch. The amount of the other ingredients contained in the antibacterial agent is not particularly limited and may be appropriately selected depending on the intended purpose so that the effects of the amycolamicin, the tautomers thereof, or the salts of the amycolamicin or the tautomers are not impaired.

The dosage form of the antibacterial agent is not particularly limited and may be appropriately selected depending on the intended purpose. Examples of the dosage form include powder, capsules, tablets and liquids. The antibacterial agent can be routinely formed into each of these dosage forms.

The administration method of the antibacterial agent is not particularly limited and may be appropriately selected depending on, for example, the dosage form of the antibacterial agent. The antibacterial agent can be administered orally or parenterally.

The dose of the antibacterial agent is not particularly limited and may be appropriately determined considering various factors of target individuals such as their age, body weight, constitution, symptoms and concomitant use of a drug containing other active ingredients.

The animal species to which the antibacterial agent is to be administered is not particularly limited and may be appropriately selected depending on the intended purpose. Examples thereof include humans, monkeys, pigs, bovines, sheep, goats, dogs, cats, mice, rats and birds.

As shown in Test Examples 1 to 4 described below, since the antibacterial agent contains as an active ingredient the amycolamicin, the tautomers thereof, or the salts of the amycolamicin or the tautomers, it has an excellent antibacterial activity against a wide variety of Gram-positive and negative bacteria such as drug-resistant bacteria and bacteria causing pneumonia in domestic livestock. Thus, the antibacterial agent can suitably used for the prevention or treatment of infectious diseases caused by pathogenic bacteria such as drug-resistant bacteria and bacteria causing pneumonia in domestic livestock as shown in Test Examples 1 to 4 described below. The antibacterial agent may be used alone or in combination with a drug containing other active ingredients. Also, the antibacterial agent may be incorporated before use into a drug containing other active ingredients.

EXAMPLES

The present invention will next be described in detail by way of Examples and Test Examples, which should not be construed as limiting the present invention thereto. In Examples and Test Examples, the unit "%" means "% by mass" unless otherwise specified.

Example 1

Production of Amycolamicin

Cells of *Amycolatopsis* sp. MK575:fF5 strain (deposited as FERM P-21465) were cultured in an agar slant medium. Separately, a liquid medium containing galactose 2%, dextrin 2%, glycerin 1%, Bacto Soytone (product of Difco Co., Ltd.) 1%, corn steep liquor 0.5%, ammonium sulfate 0.2% and calcium carbonate 0.2% (the pH of the liquid medium being adjusted to 7.4) was dispensed in 500 mL-conical flasks so that each conical flask contained 110 mL of the liquid medium, followed by routinely sterilizing at 120° C. for 20 min. The above-cultured cells were inoculated in the liquid medium. Thereafter, the cells were shake-cultured through rotation at 30° C. for 4 days, to thereby obtain seed culture liquids.

A medium (100 L) having the following composition: glycerin 0.5%, dextrin 0.5%, Bacto Soytone (product of Difco Co., Ltd.) 0.25%, yeast extract (product of NIHON PHARMACEUTICAL CO., LTD.) 0.075%, ammonium sulfate 0.05% and calcium carbonate 0.05% (the pH of the medium being adjusted to 7.4) was prepared in a 200 L-culturing tank, followed by sterilizing, to thereby obtain a production medium. Two percent by volume of each seed culture was inoculated in the production medium, followed by culturing in the tank for four days under the following conditions: 27° C., 200 rpm, air flow rate: 100 L/min.

The thus-obtained culture was centrifuged so as to be separated into 80 L of the culture filtrate and 2.5 kg of the microorganisms. Subsequently, 12 L of methanol was added to the microorganisms, and the resultant mixture was thoroughly stirred. Then, amycolamicin was extracted from the microorganisms with methanol, followed by removal of methanol under reduce pressure, to thereby obtain 2 L of a microorganism extract containing amycolamicin. Then, 6 L of ethyl acetate was added to the microorganism extract (2 L), and the resultant mixture was thoroughly stirred so that amycolamicin was extracted with ethyl acetate. The resultant mixture treated with 6 L of ethyl acetate was dried with anhydrous sodium sulfate and then concentrated and dried under reduced pressure, to thereby obtain 18 g of a crude product containing amycolamicin. Hexane (200 mL) was added to 18 g of the crude product containing amycolamicin and the hexane-soluble ingredients were removed, to thereby obtain 3.3 g of a hexane-insoluble fraction containing amycolamicin. The hexane-insoluble fraction (3.3 g) containing amycolamicin was dissolved in methanol, and the resultant solution was chromatographically separated with a Sephadex LH-20 (inner diameter: 28 mm×length: 450 mm, product of Pharmacia Biotech Inc.) column. The solution was fractionated every 8 g (one fraction) and, as a result, the active fractions were eluted as fractions 12 to 15. The fractions were collected and concentrated and dried under reduced pressure, to thereby obtain 1,584 mg of a crude product containing amycolamicin. The thus-obtained crude product (1,584 mg) was dissolved in a small amount of methanol, and 50 mL of kieselguhr (product of Merck Co.) was added to the resultant solution. Then, the solvent was concentrated and dried under reduce pressure. The kieselguhr was applied to a silica gel column (inner diameter: 32 mm×length: 175 mm, product of Merck Co.) to perform chromatography. The developing solvents sequentially used were chloroform:methanol: water=100:0:0 (200 mL), 95:5:0 (450 mL), 1:95:5=0.25 (450 mL) and 1:90:10:0.5 (450 mL). The chromatography was fractionated every 18 g (one fraction) and, as a result, amycolamicin was eluted as fractions 76 to 103. The fractions were collected and concentrated and dried under reduced pressure, to thereby obtain 827 mg of pure amycolamicin.

Through analysis of the obtained amycolamicin for physico-chemical properties, it was found to have the physico-chemical properties as shown below. From the physico-chemical properties, it was confirmed that the amycolamicin was a new compound having a structure expressed by the following Structural Formula (1). Also, this amycolamicin was found to have tautomerism.

(1) Appearance: white powder
(2) Molecular formula: $C_{44}H_{60}Cl_2N_4O_{14}$
(3) High resolution mass spectrometry (HRESIMS: negative ion mode)

Calcd: m/z 937.3386 (M-H)⁻
Found: m/z 937.3405 (as $C_{44}H_{59}Cl_2N_4O_{14}$)
(4) Specific rotation $[\alpha]_D^{23}=-21.6°$ (c0.5, methanol)
(5) Infrared absorption spectrum is as shown in FIG. 1.
(6) UV absorption spectrum is as shown in FIG. 2.
(7) $^1$H nuclear magnetic resonance (NMR) spectrum measured in deuterated methanol at 30° C. and 600 MHz is as shown in FIG. 3.
(8) $^{13}$C nuclear magnetic resonance (NMR) measured in deuterated methanol at 30° C. and 150 MHz is as shown in FIG. 4.
(9) Thin-layer chromatography using silica gel 60F$_{254}$ (product of Merck Co.) and a developing solvent of chloroform:methanol (9:1 by volume), the Rf value is 0.31.

Structural Formula (1)

Also, the obtained amycolamicin was measured for antibacterial activity in the following Test Examples 1 to 4.

Test Example 1

According to the standard method of Japanese Society of Chemotherapy, the amycolamicin was measured for antimicrobial spectrum against various microorganisms including drug-resistant bacteria (e.g., methicilline resistant bacteria and vancomycin resistant bacteria) in the Muller Hinton agar medium by the multiple dilution method. The minimum inhibitory concentrations (MICs) measured are shown in Table 1.

Test Example 2

According to the standard method of Japanese Society of Chemotherapy, the amycolamicin was measured for antimicrobial spectrum against various microorganisms including drug-resistant bacteria (e.g., penicillin resistant pneumococcus, macrolide resistant pneumococcus and penicillin resistant influenza) in the Muller Hinton agar medium supplemented with sheep blood (5% by volume) by the multiple dilution method in an atmosphere of 5% by volume $CO_2$. The minimum inhibitory concentrations (MICs) measured are shown in Table 2.

Test Example 3

According to the standard method of Japanese Society of Chemotherapy, the amycolamicin was measured for antimicrobial spectrum against bacteria causing pneumonia in domestic livestock in the brain heart infusion agar medium by the multiple dilution method. The minimum inhibitory concentrations (MICs) measured are shown in Table 3.

Test Example 4

According to the standard method of Japanese Society of Chemotherapy, the amycolamicin was measured for antimicrobial spectrum against bacteria causing pneumonia in domestic livestock other than those listed in Table 3 in the Muller Hinton agar medium supplemented with Fields enrichment (5% by volume) by the multiple dilution method in an atmosphere of 5% by volume $CO_2$. The minimum inhibitory concentrations (MICs) measured are shown in Table 4.

TABLE 1

| Tested Microorganism Strains | MIC (µg/ml) |
|---|---|
| *Staphylococcus aureus* FDA209P | 0.39 |
| *S. aureus* Smith | 0.39 |
| *S. aureus* MS9610 | 0.39 |
| *S. aureus* MRSA No.5 | 0.39 |
| *S. aureus* MRSA No.17 | 0.39 |
| *S. aureus* MS16526(MRSA) | 0.39 |
| *S. aureus* TY-04282(MRSA) | 0.39 |
| *Enterococcus faecalis* JCM 5803 | 0.2 |
| *Ent. faecalis* NCTC12201(VRE) | 0.1 |
| *Ent. faecalis* NCTC12203(VRE) | 0.2 |
| *Ent. faecium* JCM 5804 | 0.78 |
| *Ent faecium* NCTCI12202(VRE) | 0.78 |
| *Ent. faecium* NCTCI12204(VRE) | 0.78 |
| *Escherichia coli* NIHJ | 12.5 |
| *E. coli* K-12 | 12.5 |
| *Klebsiella pneumoniae* PC1602 | 6.25 |

MRSA: Methicilline resistant *Staphylococcus aureus*
VRE: Vancomycin resistant *Enterococcus*

TABLE 2

| Tested Microorganism Strains | MIC (µg/ml) |
|---|---|
| *Streptococcus pneumoniae* S-223 | 0.39 |
| *S. pneumoniae* CR-2 (PRSP) | 0.39 |
| *S. pneumoniae* T037 (PRSP) | 0.39 |
| *S. pneumoniae* H69 (PRSP) | 0.39 |
| *S. pneumoniae* KM99 (PRSP) | 0.39 |
| *S. pneumoniae* JPS326 (ermB) | 0.39 |
| *S. pneumoniae* JPS344 (ermB) | 0.20 |
| *S. pneumoniae* JPS380 (ermB) | 0.39 |
| *S. pneumoniae* JPS399 (ermB) | 0.39 |
| *S. pneumoniae* JPS408 (ermB) | 0.39 |
| *S. pneumoniae* JPS317 (mefA) | 0.39 |
| *S. pneumoniae* JPS390 (mefA) | 0.39 |
| *S. pneumoniae* JPS401 (mefA) | 0.10 |
| *S. pneumoniae* JPS402 (mefA) | 0.20 |
| *S. pneumoniae* JPS403 (mefA) | 0.20 |
| *Haemophilus infulenzae* IID938 | 0.78 |
| *H. infulenzae* IID985 | 0.78 |
| *H. infulenzae* IID986 | 0.78 |

TABLE 2-continued

| Tested Microorganism Strains | MIC (µg/ml) |
|---|---|
| H. infulenzae IID987 | 0.78 |
| H. infulenzae IID988 | 0.78 |
| H. infulenzae T196 | 0.20 |
| H. infulenzae ME570(BLNAR) | 0.78 |
| H. infulenzae ME587(BLNAR) | 0.78 |
| H. infulenzae ME870(BLNAR) | 0.78 |
| H. infulenzae MT066(BLNAR) | 0.78 |
| H. infulenzae ARD476(BLPAR) | 0.78 |

PRSP: Penicillin resistant *Streptococcus pneumiae*
ermB: Macrolide resistant *Streptococcus pneumiae*
mefA: Macrolide resistant *Streptococcus pneumiae*
BLNAR: Beta-lactamase-nonproducing penicillin resistant *Haemophilus influenza*
BLPAR: Beta-lactamase-producing penicillin resistant *Haemophilus influenza*

TABLE 3

| Tested Microorganisms | Strains | MIC (µg/ml) |
|---|---|---|
| Mannheimia haemolytica | N791 | 0.78 |
| M. haemolytica | N811 | 0.78 |
| Pasteurella multocida | No. 6 | 1.56 |
| P. multocida | Kobe | 0.78 |
| P. multocida | TS-8 | 0.78 |
| P. multocida | M-17 | 0.78 |

TABLE 4

| Tested Microorganisms | Strains | MIC (µg/ml) |
|---|---|---|
| Actinobacillus pleuropneumoniae | NB001 | 1.56 |
| A. pleuropneumoniae | YN | 0.78 |
| A. pleuropneumoniae | SHP-17 | 1.56 |
| A. pleuropneumoniae | CH-1 | 1.56 |
| A. pleuropneumoniae | CH-2(H4024) | 1.56 |
| A. pleuropneumoniae | M-1 | 0.78 |
| A. pleuropneumoniae | O-223 | 1.56 |
| A. pleuropneumoniae | Shop1421 | 3.13 |
| A. pleuropneumoniae | HPT-1 | 1.56 |
| A. pleuropneumoniae | Hi-1 | 3.13 |
| A. pleuropneumoniae | 6H-8 | 1.56 |
| A. pleuropneumoniae | 7H-3 | 1.56 |
| Histophilus somni | 23N2359 | 0.20 |

From the results of Tables 1 to 4, the amycolamicin was found to exhibit an excellent antibacterial activity against Gram-positive and negative bacteria such as drug-resistant bacteria and bacteria causing pneumonia in domestic livestock. Among others, the amycolamicin was found to exhibit a particularly excellent antibacterial activity against *Staphylococcus aureus* including MRSA, *Enterococcus faecalis/faecium* including VRE, *Streptococcus pneumoniae* including macrolide resistant bacteria and penicillin resistant bacteria, *Haemophilus infulenzae* including penicillin resistant bacteria, *Mannheimia haemolytica*, *Pasteurella multocida* and *Histophilus somni*.

INDUSTRIAL APPLICABILITY

The new compound (amycolamicin) of the present invention, the tautomers thereof or the salts of the compound (amycolamicin) or the tautomers have an excellent antibacterial activity against a wide variety of pathogenic bacteria such as drug-resistant bacteria and bacteria causing pneumonia in domestic livestock and thus can suitably used as an antibacterial agent.

| | | |
|---|---|---|
| 0-1 | Form PCT/RO/134 (SAFE) Indications Relating to Deposited Microorganism(s) or Other Biological Material (PCT Rule 13bis) | |
| 0-1-1 | Prepared Using | JPO-PAS 0361 |
| 0-2 | International Application No. | |
| 0-3 | Applicant's or agent's file reference | N-BK001-09P |
| 1 | The indications made below relate to the deposited microorganism(s) or other biological material referred to in the description on: | |
| 1-1 | Paragraph number | 0032 |
| 1-3 | Identification of deposit | |
| 1-3-1 | Name of depositary institution | IPOD National Institute of Advanced Industrial Science and Technology, International Patent Organism Depositary |
| 1-3-2 | Address of depositary institution | Tsukuba Central 6, 1-1-1 Higashi, Tsukuba, Ibaraki, 305-8566 Japan |
| 1-3-3 | Date of deposition | Dec. 12, 2007 (12. 12. 2007) |
| 1-3-4 | Accession Number | IPOD FERM P-21465 |
| 1-5 | Designated States for Which Indications are Made | All designations |

| | | |
|---|---|---|
| 0-4 | This form was received with the international application: | |
| 0-4-1 | Authorized officer | |

| | | |
|---|---|---|
| 0-5 | This form was received by the international Bureau on: | |
| 0-5-1 | Authorized officer | |

What is claimed is:

1. A compound having a structure expressed by the following Structural Formula (1), tautomers thereof, or salts of the compound or the tautomers Structural Formula (1)

2. A method for producing a compound having a structure expressed by the following Structural Formula (1), tautomers thereof, or salts of the compound or the tautomers, the method comprising:
    culturing a microorganism belonging to the genus *Amycolatopsis* and capable of producing the compound having a structure expressed by the Structural Formula (1), the tautomers thereof, or the salts of the compound or the tautomers, and
    isolating the compound having a structure expressed by the Structural Formula (1), the tautomers thereof, or the salts of the compound or the tautomers from a culture obtained from the culturing

Structural Formula (1)

3. The method according to claim 2, wherein the microorganism is a microorganism of *Amycolatopsis* sp. MK575-fF5 strain deposited under accession number FERM P-21465.

4. A microorganism,
    wherein the microorganism belongs to the genus *Amycolatopsis* and is capable of producing a compound having a structure expressed by the following Structural Formula (1), tautomers thereof, or salts of the compound or the tautomers Structural Formula (1)

5. The microorganism according to claim 4, wherein the microorganism is a microorganism of *Amycolatopsis* sp. MK575-fF5 strain deposited under accession number FERM P-21465.

6. An antibacterial agent comprising:
a compound having a structure expressed by the following Structural Formula (1), tautomers thereof, or salts of the compound or the tautomers, serving as an active ingredient Structural Formula (1)